(12) United States Patent
Rathke et al.

(10) Patent No.: US 9,448,215 B2
(45) Date of Patent: Sep. 20, 2016

(54) OPTICAL GAS ANALYZER DEVICE HAVING MEANS FOR CALIBRATING THE FREQUENCY SPECTRUM

(71) Applicant: ABB AG, Mannheim (DE)

(72) Inventors: Carsten Rathke, Schöneck (DE); Gerhard Thielemann, Eschborn (DE); Norbert Will, Nidderau (DE); Werner Rüdiger, Mühltal (DE)

(73) Assignee: ABB AG, Mannheim (DE)

( * ) Notice: Subject to any disclaimer, the term of this patent is extended or adjusted under 35 U.S.C. 154(b) by 428 days.

(21) Appl. No.: 13/925,505

(22) Filed: Jun. 24, 2013

(65) Prior Publication Data
US 2013/0276509 A1    Oct. 24, 2013

Related U.S. Application Data

(63) Continuation of application No. PCT/EP2011/006483, filed on Dec. 21, 2011.

(30) Foreign Application Priority Data

Dec. 23, 2010    (DE) .................. 10 2010 056 137

(51) Int. Cl.
*G01N 33/00* (2006.01)
*G01N 21/27* (2006.01)
(Continued)

(52) U.S. Cl.
CPC ........ *G01N 33/0006* (2013.01); *G01N 21/276* (2013.01); *G01N 21/278* (2013.01); *G01N 21/3504* (2013.01); *G01N 21/61* (2013.01)

(58) Field of Classification Search
None
See application file for complete search history.

(56) References Cited

U.S. PATENT DOCUMENTS 3,825,756 A    7/1974  Weiss
5,060,505 A *  10/1991 Tury et al. .............. 250/343
(Continued)

FOREIGN PATENT DOCUMENTS

DE              35 22 949 A1    1/1987
DE        10 2009 025 147    * 12/1992
(Continued)

OTHER PUBLICATIONS

International Search Report (PCT/ISA/210) issued on Apr. 25, 2012, by the European Patent Office as the International Searching Authority for International Application No. PCT/EP2011/006483.
(Continued)

*Primary Examiner* — Robert R Raevis
(74) *Attorney, Agent, or Firm* — Taft Stettinius & Hollister LLP

(57) ABSTRACT

Exemplary embodiments relate to an optical gas analyzer device that includes at least one measuring chamber in the form of a tubular measuring cuvette through which measuring gas flows. The measuring chamber is illuminated longitudinally by a radiation source that is arranged at an input end thereof and the light beam of which weakened by absorption losses is detected for gas concentration analysis by at least one detector arranged at an output end. The measuring process is calibrated using a reference spectrum. A special optical filter can be inserted into the measuring process in place of the measuring cuvette. The filter material of the filter generates a plurality of strong absorptions across the entire wavelength range of the measuring spectrum in order to cause attenuations that in the particular spectral position correspond to those of the gaseous measuring medium in greater concentration.

13 Claims, 2 Drawing Sheets

(51) Int. Cl.
  *G01N 21/3504* (2014.01)
  *G01N 21/61* (2006.01)

(56) References Cited

U.S. PATENT DOCUMENTS

| | | | |
|---|---|---|---|
| 5,067,492 A * | 11/1991 | Yelderman et al. | 600/532 |
| 5,125,747 A | 6/1992 | Sayegh et al. | |
| 5,334,536 A | 8/1994 | Nonnenmacher | |
| 5,616,823 A | 4/1997 | Lattimore | |
| 5,739,535 A * | 4/1998 | Koch et al. | 250/339.13 |
| 5,793,044 A * | 8/1998 | Mace et al. | 250/343 |
| 6,006,585 A * | 12/1999 | Forster | 73/24.01 |
| 6,594,008 B1 * | 7/2003 | Herpst et al. | 356/243.1 |
| 6,710,347 B1 * | 3/2004 | Eden | 250/343 |
| 2010/0282958 A1 | 11/2010 | Will et al. | |

FOREIGN PATENT DOCUMENTS

| | | |
|---|---|---|
| DE | 41 19 346 A1 | 12/1992 |
| DE | 295 21 226 U1 | 10/1996 |
| DE | 691 27 670 T2 | 4/1998 |
| DE | 10 2007 056345 B3 | 1/2009 |
| WO | WO 2010/145809 A1 | 12/2010 |

OTHER PUBLICATIONS

Written Opinion (PCT/ISA/237) issued on Apr. 25, 2012, by the European Patent Office as the International Searching Authority for International Application No. PCT/EP2011/006483.

German Examination Report for 10 2010 056 137.1 dated Mar. 19, 2012.

* cited by examiner

OPTICAL GAS ANALYZER DEVICE HAVING MEANS FOR CALIBRATING THE FREQUENCY SPECTRUM

RELATED APPLICATION(S)

This application is a continuous under 35 U.S.C. §120 of PCT/EP2011/006483 filed as an International application on Dec. 21, 2011, designating the U.S. and claiming priority to German application DE1020/0056137.1 filed in Germany on Dec. 23, 2010. The content of each prior application is hereby incorporated by reference in its entirety.

FIELD

The disclosure relates to an optical gas analyzer device, including at least one measurement chamber, through which measurement gas flows and which is formed in a tubular measurement cuvette and which is illuminated longitudinally by means of a radiation source arranged at the input end, the light beam of which, attenuated by absorption losses, is captured for gas concentration analysis by at least one detector arranged at the output end, wherein means for calibrating the measurement path are provided in the form of a reference spectrum.

BACKGROUND INFORMATION

In order to set precisely the zero point and the sensitivity of an optical gas analyzer device, use can be made of a so-called zero gas or test gas with a known concentration, which flows through the measurement space during the calibration. As a result, the detector unit records a measured value, which is brought into correspondence with an expected intended value for calibration purposes. This known method can be used to undertake a largely precise sensitivity calibration, which removes a drift, which was, for example, caused by changes in the transmission behavior. This method is the only way to ensure the reliability of the measurement result over time. In the case of easily manageable gas components, such as carbon monoxide or carbon dioxide, this procedure can be carried out easily; in known implementations, it can be more difficult to calibrate a gas analyzer device for other gases such as nitrogen oxides, hydrochloric acid, water vapor.

The advantage of optical gas analyzer devices, on the other hand, is that many gas components can be measured at the same time. Hence, such instruments can also be suitable for emission measurements. The gas analyzer device can be checked regularly. Here, the calibration data are, in practice, checked in two steps. A reference spectrum with zero gas, for example, ambient air, is recorded regularly at short intervals, e.g., daily. This reference spectrum can be used to compensate for changes in the transmission behavior of the measurement system. Changes in the transmission behavior can, for example, be caused by changes in the radiation source or the detector, or else by contamination of the measurement chamber. The zero point is compensated for in a wavelength-dependent fashion, so that the zero point is corrected at the same time for all components.

In a further step, that can be carried out weekly to yearly, there is a regular check and, in other exemplary embodiments as desired, a calibration of the reference points for all components using a test gas. Easily manageable gases can be calibrated without additional aids using test gases from test-gas flasks. Test-gas generators are used in place of test-gas flasks in the case of gases that are difficult to manage, which test-gas generators have a relatively complex design and are difficult to operate at some locations where gas analyzer devices are used.

DE 35 22 949 A1 has disclosed an optical gas analyzer device, the calibration of which is brought about by means of test gas. The gas analyzer device operating according to the NDIR method substantially consists of a radiation source for infrared light, which passes through the one end-side window of a measurement cuvette including the measurement chamber and through the other end-side window in a comparison cuvette arranged in parallel. The measurement gas flows through the measurement cuvette, for the purposes of which an inlet port and outlet port is provided on the latter. The measurement cuvette is spatially separated from the comparison cuvette, and so the gas analyzer device has two beam paths. The light rays entering the measurement cuvette and the comparison cuvette are modulated in anti-phase by a rotating interrupter wheel. The measurement beam leaves the measurement cuvette through an output-end window and the comparison beam passes through another output-end window arranged adjacent thereto. Measurement beam and comparison beam are recorded by an opto-pneumatic detector. The front side of the detector is closed-off with the aid of an infrared-transmissive window.

Since the gas analyzer device should still supply reliable measured value, even after a relatively long time, there has to be a readjustment within the meaning of a calibration. This is brought about with the aid of an adjustment apparatus, which has a carriage arrangement, the latter holding two pairs of calibration cuvettes. While one pair of calibration cuvettes is completely filled with an inert gas, the other pair of calibration cuvettes is such that one calibration cuvette is filled with an inert gas while the other the calibration cuvette of this pair is filled with the measurement component. If carbon dioxide should be analyzed with the aid of the gas analyzer device, the measurement cuvette is filled with carbon dioxide. Said carriage arrangement can be moved to-and-fro. In the end position, the two calibration cuvettes filled with inert gas are situated in the measurement path. The zero point is calibrated in this position. If the guide arrangement is in the other end position, the other pair of unequal measurement cuvettes is situated in the measurement path. This can be used to adjust the endpoint or the sensitivity of the measurement arrangement. This solution for calibrating the measurement path is particularly suitable for cleaned carbon dioxide-free and water vapor-free test gases. However, the technical means for calibrating the measurement path, such as the various measurement cuvettes, for example, appear to be relatively complex.

Another gas analyzer device which is disclosed in DE 10 2007 065345 B3, operates on the principles of FTIR spectroscopy. Proceeding from a radiation source, a first optical system is used to generate a parallel beam by widening, which beam is incident on a semi-transparent mirror, which acts as a beam splitter. Some of the light with a fixed wavelength and frequency position, e.g., monochromatic and coherent light, is now incident on a fixed mirror and is reflected there. The other partial light beam passes through the semi-transparent mirror in a straight line and is reflected back by a movable rear mirror in the direction of the semi-transparent mirror, where these two partial light beams now interfere with one another. Here, the interference is governed in a controllable fashion by moving the rear mirror along the optical axis. From there, the interfering light passes through a measurement cuvette through which measurement gas is conducted. The interferometer achieves very precise tuning of the effective frequency position of the light beam impinging on the measurement cuvette and hence the measurement gas. Hence, a complex spectrum can be detected at the detector, and not only the absorption rate at a fixed frequency. In order to illuminate the detector optically, the split light beam is refocused by a second optical system, to be precise to the dimensions of the detector.

In order to calibrate the measurement system, it can be possible for calibration gas to be conducted through the measurement cuvette so as to reintroduce the measurement gas after the calibration step by reversing valves. As an alternative to this, a proposal suggests, optionally, to restrict the calibration gas with the aid of calibration cuvettes in the measurement path in front of the detector, to be precise for as long as the calibration or validation takes. The calibration cuvette can be thereafter pivoted out of the beam path again. The calibration cuvette is filled with a replacement gas or replacement gas mixture representing the spectrum of the measurement gas. Thus, sulfur dioxide, carbon dioxide or the like can be used as representatives of the spectral range in place of the gas components hydrochloric acid, water vapor and the like, which can be more difficult to manage.

The validation or calibration of the reference points of a gas analyzer device can, for example, if this relates to the aforementioned gases that are difficult to manage, only be carried out with great technical complexity and a high expenditure of time. This is because, additional technical equipment, such as a test-gas generator, can be installed and the gases that are difficult to manage specify a long setting time. A calibration or validation of the reference points can therefore only be carried out by educated specialists. The reference points are therefore only checked after long intervals; e.g., there is no validation of the reference points for relatively long measurement intervals. This leads to an increased risk of an erroneous evaluation of measured gas concentrations.

In this manner, it is possible to dispense with the use of a complicated test generator in the case of gases that are difficult to manage; however, it can be beneficial to provide the calibration cuvettes filled with the replacement gas.

High quality specifications are to be placed on the manufacturing process thereof in order to ensure a precise calibration. Furthermore, care has to be taken that the gases are chemically compatible amongst themselves and with the materials of the calibration cuvettes. Furthermore, the calibration cuvettes can be filled with a very high partial pressure in order to obtain a product of concentration multiplied by absorption wavelength which corresponds to that in the long path cell of an FTIR spectrometer.

SUMMARY

An exemplary optical gas analyzer device is disclosed comprising: at least one measurement chamber through which measurement gas flows being formed in a tubular measurement cuvette and illuminated longitudinally by means of a radiation source arranged at an input end; at least one detector arrangement at an output end and configured to capture a light beam of the radiation source for gas concentration analysis, wherein a reference spectrum is used to calibrate a measurement path; and an optical filter configured to be inserted into the measurement path in place of the measurement cuvette as means for calibration, the optical filter includes filter material that generates a multiplicity of absorptions over an entire wavelength range of a measurement spectrum in order to cause attenuations which, in a respective spectral position, correspond to attenuations of the gaseous measurement medium in a specified concentration.

An exemplary non-transitory computer readable medium is disclosed having recorded therein program code for a method of calibrating a measurement system, the computer readable medium when placed in communicable contact with a processor causes the processor to execute a method comprising: evaluating a measurement signal; and calculating a gas concentration value based on the evaluation.

BRIEF DESCRIPTION OF THE DRAWINGS

Further measures which improve the disclosure will be explained in more detail below on the basis of the figures, together with a description of an exemplary embodiment of the disclosure. In detail.

DETAILED DESCRIPTION

Figure 1:
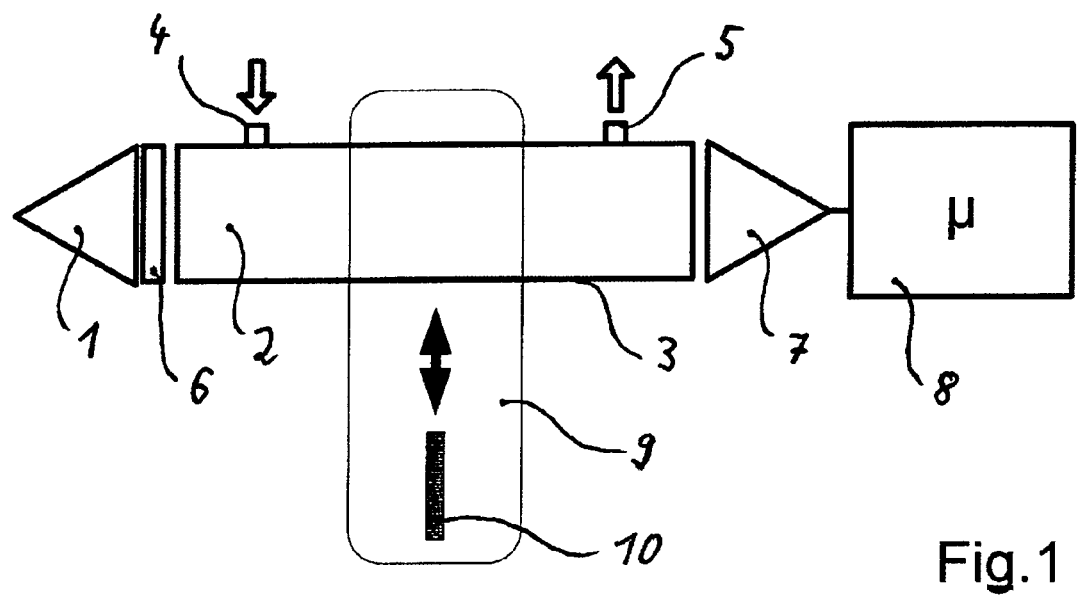
FIG. 1 shows a schematic illustration of an optical gas analyzer device with a special optical filter as means for calibrating the measurement path.

Exemplary embodiments of the present invention extend to industrial applications, in which the concentration of a gas in a gas mixture should be determined. Here, the gas concentration is measured by means of absorption of electromagnetic radiation. The optical gas analyzer device of interest can operate according to the principle of ultraviolet resonance absorption spectroscopy for nitrogen oxide analysis; however, it can also be used according to a measurement principle of the non-dispersive ultraviolet absorption for establishing the gas concentration of sulfur dioxide or nitrogen dioxide in a desired ultraviolet spectral range from 200 to 600 nanometers. In addition, it is also feasible to apply exemplary embodiments disclosed herein to infrared photometers, which operate according to the measurement principle of the non-dispersive infrared absorption wavelength range from 2.5 to 8 micrometers. Here, the radiation absorption is a measure for the concentration of the measurement medium to be measured, which brings about the absorption, or a component thereof. To this end, the measurement medium flows through the measurement chamber in the longitudinal direction, wherein window openings for the photometric measurement path of the light beam are provided at the end side of the measurement chamber, which usually has a cylindrical design.

Exemplary embodiments of the present disclosure develop an optical gas analyzer device, the means of which for calibrating the measurement path have a simple design and enable precise adjustment.

Exemplary embodiments of the present disclosure provide that an optical filter is inserted into the measurement path in place of the measurement cuvette as means for calibrating the measurement path, the special filter material of which filter generates a multiplicity of strong absorptions over the whole wavelength range of the measurement spectrum in order to cause attenuations which, in the respective spectral position, correspond to those of the gaseous measurement medium in a high concentration.

The advantage of the solution according to the disclosure particularly lies in the fact that it is possible to dispense completely with calibration cuvettes or even more complicated test-gas generators for calibration purposes. The calibration or validation is not brought about on the basis of a comparison gas produced by whatever means specified, but on the basis of a solid body, which is embodied here as an optical filter, e.g., as a type of semi-transparent disk.

In accordance with an exemplary embodiment of the present disclosure, it is proposed that the special optical filter with the complex absorption spectrum is made from polystyrene film. Such films are available as bulk commodity in various thicknesses and diameters. In an exemplary embodiment, the special optical filter can be made of polystyrene films with a thickness between, for example, 10 micrometers to 100 micrometers, and according to an exemplary embodiment at 50 micrometers. In the infrared spectral range, such films have numerous pronounced absorption bands which correlate strongly with the absorptions of nitrogen oxides, hydrochloric acid, water vapor and the like. It is precisely these gas molecules which to a large part cannot be stored in a long-term stable state in a calibration cuvette. As a result, the process of pivoting polystyrene film into the measurement path provides a simple and reliable validation option for the measurement system.

For use at other wavelengths or for other gas components, filter materials should be used in the optical filter, which filter materials consist of a polymer film, which can be selected from the material group including polyethylene terephthalate (PET), polyvinyl fluoride (PVF), polypropylene (PP), polyethylene (PE), polyimide (PI), polyisobutylene (FIB), bisphenol A (BPA), epichlorohydrin, polyarcrylate, polyamide (PA), polycarbonate, polychloroprene, polyisoprene, polyvinyl acetate, polyvinyl alcohol, polyvinyl chloride, silicone and styrene-butadiene.

In principle, specially developed optical interference filters can also be considered for developing an optical filter with strong absorptions over the wavelength range of the measurement spectrum for calibration purposes.

In accordance with an exemplary embodiment disclosure herein, thin films can be affixed to a substrate. This allows said films to be stabilized in terms of their position and alignment in relation to the measurement path. By way of example, calcium fluoride can be used as a substrate. It is also feasible to assemble a plurality of films one behind the other on a common substrate as a film carrier and introduce these into the measurement path at the same time in order to generate a sum spectrum of these individual films forming the optical filter.

Thus, the optical filter can consist of a plurality of individual films arranged next to one another, which have different spectral transmission curves. Such a combination makes it possible to generate complex absorption spectra in a simple manner. In another exemplary embodiment, an optical filter consisting of films can be combined with a known gas-filled adjustment cuvette. This alternative can be considered if it is not possible to use films to reproduce the characteristic absorption bands of the measurement spectrum.

In accordance with still another exemplary embodiment of the disclosure, it is proposed that a pivoting-in device, which is arranged to the side of the measurement path, is used for replaceable pivoting-in of the optical filter in place of the measurement cuvette. By using such a pivoting-in device, it is possible to replace the measurement cuvette with the optical filter in a precise and quick manner. In the simplest case, the pivoting-in device can be formed from a rotationally mounted jib drum, which carries the optical filter on one side and the measurement cuvette on the other side. The pivoting-in per se can be brought about in a manual or motor-controlled fashion. In the latter case, a sensor system should be present for positioning the optical filter or the measurement cuvette into place.

In accordance with an exemplary embodiment of the present disclosure, the gas analyzer device includes (e.g., comprises) an electronic evaluation unit, which, after pivoting the optical filter into the measurement path in place of the measurement cuvette, carries out an evaluation algorithm for calibrating the measurement system in place of a measurement algorithm for calculating the gas concentration. Both the evaluation algorithm and the measurement algorithm can be executed here in the form of software in a microprocessor-controlled evaluation unit. Since the evaluation algorithm differs from the actual measurement algorithm, there is the option of, by a simple algorithm interchange, undertaking a highly precise calibration of the measurement system within a short period of time.

The optical gas analyzer device according to the present disclosure is suitable for gas analysis on the basis of FTIR, NDUV or NDIR spectroscopy and can, to this extent, be used universally for gas analysis.

FIG. 1 shows a schematic illustration of an optical gas analyzer device with a special optical filter as means for calibrating the measurement path. In accordance with FIG. 1, the gas analyzer device, embodied as an NDIR includes an optical radiation source 1 for infrared light, which radiates longitudinally through a measurement chamber 2 formed by a measurement cuvette 3. The measurement cuvette 3 has an input 4 for measurement gas flowing in and an output 5 for measurement gas flowing out.

The infrared light rays entering the measurement cuvette 3 are guided through a pre-filter 6 arranged between the radiation source 1 and the measurement cuvette 3. Within the measurement chamber 2, the light ray experiences attenuation as a result of absorption losses, which attenuation is captured by an optical detector 7 arranged at the output end of the measurement cuvette 3. The detector 7 supplies an electrical signal corresponding to the measured value, which signal is provided on the input side of an electronic evaluation unit 8. The electronic evaluation unit 8 evaluates the measurement signal with the aid of an implemented measurement algorithm for calculating the gas concentration. The gas concentration value established thus can be output in a known manner.

The optical gas analyzer device furthermore includes a pivoting-in device 9, which in this case is embodied in the style of a carriage arrangement and serves for interchangeable pivoting-in of an optical filter 10 in place of the measurement cuvette 3. For this purpose, the pivoting-in device 9 can be actuated by hand in this exemplary embodiment in order to bring about the above-described change between measurement cuvette 3 and optical filter 10.

Figures 2A, 2B, 2C:
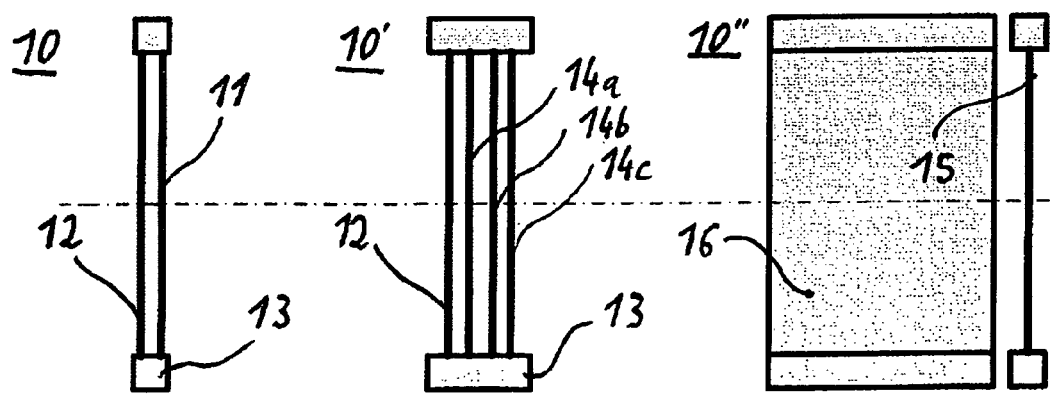
FIG. 2A shows a first optical filter in accordance with an exemplary embodiment of the present disclosure.
FIG. 2B shows a second optical filter in accordance with an exemplary embodiment of the present disclosure.
FIG. 2C shows a third optical filter in accordance with an exemplary embodiment of the present disclosure.

FIG. 2A shows a first optical filter in accordance with an exemplary embodiment of the present disclosure. In accordance with FIG. 2A, the optical filter 10 consists of a single polystyrene film 11 with a thickness of 50 micrometers. In order to stabilize the polystyrene film 11 in relation to the measurement path indicated by the dash-dotted line, provision is made for a completely IR-transmissive substrate 12 on which the polystyrene film 11 is affixed. Furthermore, the optical filter 10 is surrounded by a holding ring 13 made of metal, which establishes the mechanical connection to the pivoting-in device 9 (not illustrated in any more detail).

FIG. 2B shows a second optical filter in accordance with an exemplary embodiment of the present disclosure. According to the exemplary embodiment shown in FIG. 2B, the optical filter 10' consists of a total of three individual polymer films 14a to 14c arranged next to one another, which films are in this case likewise affixed by substrate 12 and have different spectral transmission curves, which, in combination, correspond to the desired measurement spectrum.

FIG. 2C shows a third optical filter in accordance with an exemplary embodiment of the present disclosure. In accordance with FIG. 2C, an optical filter 10" made of a single film 15—such as polystyrene film—is combined with a known gas-filled adjustment cuvette 16 in order to cover a specific measurement spectrum for calibration purposes.

Figure 3:
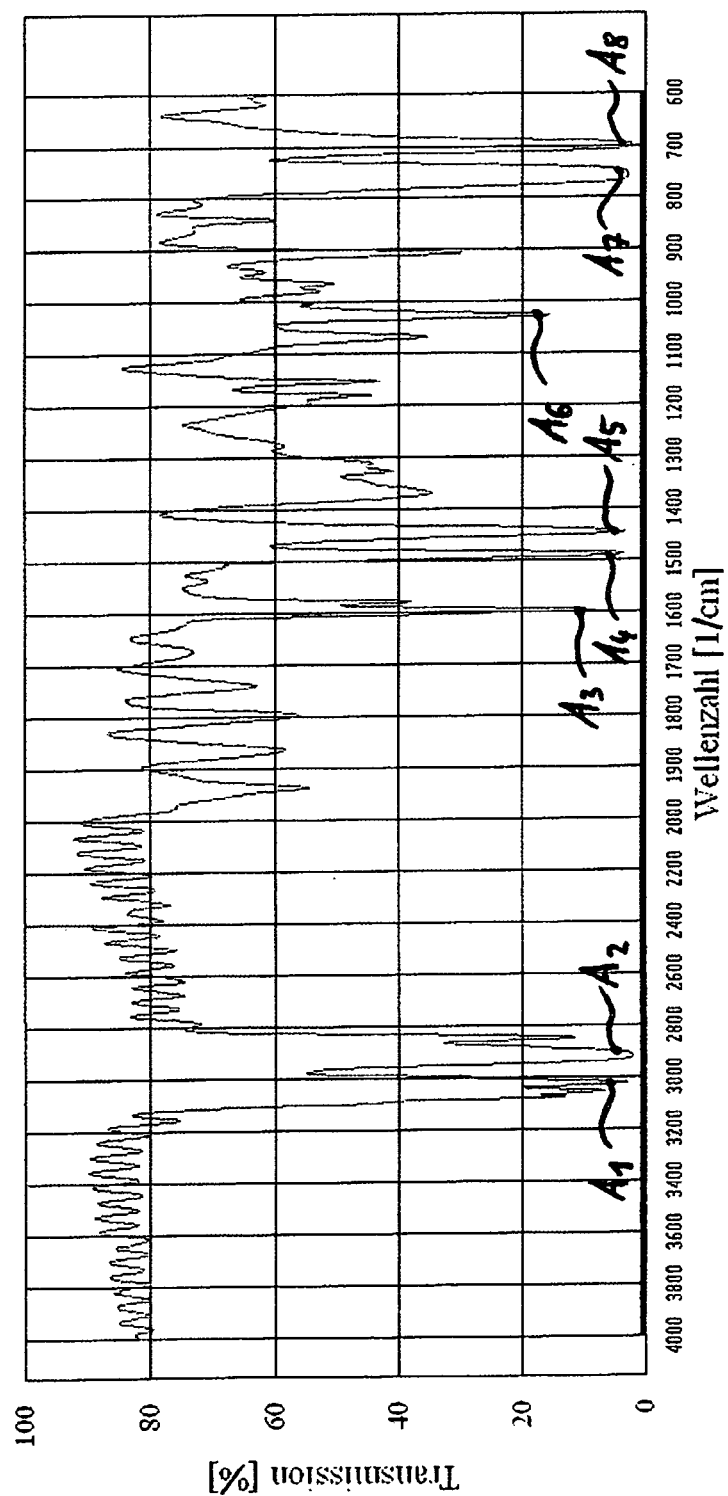
FIG. 3 shows a graph of the transmission of an optical filter over the wavelength range.

FIG. 3 shows a graph of the transmission of an optical filter over the wavelength range. In FIG. 3, the absorption spectrum of a polystyrene film with a thickness of 50 micrometers as an optical filter is illustrated, which spectrum covers a wavenumber between 600 to 4000 1/cm. This filter material causes a plurality of attenuations A1 to A8, which, in the respective spectral position, correspond to those of the gaseous measurement medium in a sufficiently high concentration.

The disclosure is not restricted to the above-described exemplary embodiments. Rather, developments of this, which also comprise the scope of protection of the subsequent claims, are also conceivable. By way of example, it is thus also possible to provide the optical filter for calibrating the gas analyzer device with a different filter material, provided this can cover the desired measurement spectrum.

In another exemplary embodiment, an evaluation algorithm or measurement algorithm can be implemented in the form of a computer program product that is recorded as software or program code on a data medium or non-transitory computer readable medium. As already discussed, the evaluation algorithm can be configured to calibrate the measurement system. The measurement algorithm can be configured to calculate the gas concentration. The evaluation algorithm and the measurement algorithm can be executed in the electronic evaluation unit 8 through control commands generated through the software or program code.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

LIST OF REFERENCE SIGNS

1 Radiation source
2 Measurement chamber
3 Measurement cuvette
4 Input
5 Output
6 Pre-filter
7 Detector
8 Electronic evaluation unit
9 Pivoting-in device
10 Optical filter
11 Polystyrene film
12 Substrate
13 Holding ring
14 Films (arranged next to one another)
15 Film (individually)
16 Adjustment cuvette
$A_n$ $n^{th}$ attenuation

What is claimed is:

1. An optical gas analyzer device comprising:
   at least one measurement chamber through which measurement gas flows being formed in a tubular measurement cuvette and illuminated longitudinally by means of a radiation source arranged at an input end;
   at least one detector arrangement at an output end and configured to capture a light beam of the radiation source for gas concentration analysis, wherein a reference spectrum is used to calibrate a measurement path; and
   an optical filter configured to be inserted into the measurement path in place of the measurement cuvette as means for calibration, the optical filter includes filter material that generates a multiplicity of absorptions over an entire wavelength range of a measurement spectrum in order to cause attenuations which, in a respective spectral position, correspond to attenuations of the gaseous measurement medium in a specified concentration,
   wherein the optical filter comprises at least one gas-filled adjustment cuvette in addition to at least one film.

2. The optical gas analyzer device as claimed in claim 1, wherein the filter material of the at least one film of the optical filter consists of a polystyrene film.

3. The optical gas analyzer device as claimed in claim 2, wherein the polystyrene film has a thickness in a range between 10 micrometer to 100 micrometer.

4. The optical gas analyzer device as claimed in claim 3, wherein the polystyrene film has a thickness of 50 micrometers.

5. The optical gas analyzer device as claimed in claim 1, wherein the filter material of the at least one film of the optical filter is selected from a material group including:
   polyethylene terephthalate (PET), polyvinyl fluoride (PVF), polypropylene (PP), polyethylene (PE), polyimide (PI), polyisobutylene (PIB), bisphenol A (BPA), epichlorohydrin, polyarcrylate, polyamide (PA), polycarbonate, polychloroprene, polyisoprene, polyvinyl acetate, polyvinyl alcohol, polyvinyl chloride, silicone and styrene-butadiene.

6. The optical gas analyzer device as claimed in claim 1, wherein the optical filter is configured to be pivoted into the measurement path comprising:
   an electronic evaluation unit, which after pivoting the optical filter into the measurement path in place of the measurement cuvette, is configured to carry out an evaluation algorithm for calibrating the measurement system in place of a measurement algorithm for calculating the gas concentrations.

7. The optical gas analyzer device as claimed in claim 1, wherein a gas analysis takes place on the basis of FTIR, NDUV or NDIR spectroscopy.

8. An optical gas analyzer device comprising:
   at least one measurement chamber through which measurement gas flows being formed in a tubular measurement cuvette and illuminated longitudinally by means of a radiation source arranged at an input end;
   at least one detector arrangement at an output end and configured to capture a light beam of the radiation source for gas concentration analysis, wherein a reference spectrum is used to calibrate a measurement path; and an optical filter configured to be inserted into the measurement path in place of the measurement cuvette as means for calibration, the optical filter includes filter material that generates a multiplicity of absorptions over an entire wavelength range of a measurement spectrum in order to cause attenuations which, in a respective spectral position, correspond to attenuations of the gaseous measurement medium in a specified concentration, wherein a pivoting-in device is provided to the side of the measurement path for replaceable pivoting-in of the optical filter in place of the measurement cuvette.

9. The optical gas analyzer device as claimed in claim 8, wherein the at least one film of the optical filter includes film that is affixed to a substrate for stabilization purposes.

10. The optical gas analyzer device as claimed in claim 9, wherein the at least one film of the optical filter includes a plurality of individual films arranged next to one another, and having different spectral transmission curves.

11. The optical gas analyzer device as claimed in claim 8, wherein the at least one film of the optical filter includes a plurality of individual films arranged next to one another, and having different spectral transmission curves.

12. The optical gas analyzer device as claimed in claim 11, wherein the at least one film of the optical filter includes film that is affixed to a substrate for stabilization purposes.

13. A non-transitory computer readable medium having recorded therein program code for a method of calibrating a measurement system having:
- at least one measurement chamber through which measurement gas flows being formed in a tubular measurement cuvette and illuminated longitudinally by means of a radiation source arranged at an input end;
- at least one detector arrangement at an output end and configured to capture a light beam of the radiation source for gas concentration analysis, wherein a reference spectrum is used to calibrate a measurement path; and
- an optical filter configured to be inserted into the measurement path in place of the measurement cuvette as means for calibration, the optical filter includes filter material that generates a multiplicity of absorptions over an entire wavelength range of a measurement spectrum in order to cause attenuations which, in a respective spectral position, correspond to attenuations of the gaseous measurement medium in a specified concentration,
- wherein the optical filter comprises at least one gas-filled adjustment cuvette in addition to at least one film, the computer readable medium when placed in communicable contact with a processor causes the processor to execute a method comprising:

evaluating a measurement signal; and calculating a gas concentration value based on the evaluation.

* * * * *